(12) United States Patent
Sang et al.

(10) Patent No.: US 8,426,220 B2
(45) Date of Patent: Apr. 23, 2013

(54) UTILIZATION OF SHIELD EFFECT FOR DOPAMINE DETECTION AND REAGENT DEVELOPMENT

(75) Inventors: Tzu-Kang Sang, Hsinchu (TW); Cheng-Yuan Lin, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 339 days.

(21) Appl. No.: 12/723,969

(22) Filed: Mar. 15, 2010

(65) Prior Publication Data
US 2010/0284988 A1 Nov. 11, 2010

(30) Foreign Application Priority Data
May 5, 2009 (TW) .............................. 98114788 A

(51) Int. Cl.
*G01N 33/566* (2006.01)
(52) U.S. Cl.
USPC .......... 436/501; 424/9.6; 424/94.3; 424/94.4; 436/63; 436/86; 436/172; 436/815; 530/402

(58) Field of Classification Search ........................ None
See application file for complete search history.

(56) References Cited

PUBLICATIONS

Rebrin, I. et al; "Effects of carboxyl terminal truncations on the activity and solubility of human monoamine oxidase B." J. Bio. Chem. (2001) 276(31) p. 29499-29506.*
Min Li et al.,Functional Role of the "Aromatic Cage" in Human Monoamine Oxidase B:Structures and Catalytic Properties of Tyr435 Mutant Proteins, Biochemistry 2006, 45, 4775-4784.

* cited by examiner

*Primary Examiner* — Cecilia J Tsang
*Assistant Examiner* — Fred Reynolds
(74) *Attorney, Agent, or Firm* — WPAT, P.C.; Anthony King

(57) ABSTRACT

The present invention relates to fusion proteins of monoamine oxidase B (MAO B)-green fluorescent protein (GFP) and utilizes "shield effect" to detect the dopamine under physiological condition, providing the reagent and method for dopamine detection.

14 Claims, 12 Drawing Sheets
(8 of 12 Drawing Sheet(s) Filed in Color)

*Biochemistry* 2006, *45*, 4777

UTILIZATION OF SHIELD EFFECT FOR DOPAMINE DETECTION AND REAGENT DEVELOPMENT

FIELD OF THE INVENTION

The present invention utilizes shield effect to generate fusion proteins of monoamine oxidase B (MAO B)-green fluorescent protein (GFP) for detecting dopamine under physiological condition and providing related analytical reagent and method.

BACKGROUND OF THE INVENTION

Dopamine is a crucial neurotransmitter in the nervous system that regulates activities including movement, olfaction, and mood. Dopamine is derived from tyrosine via a series of enzyme-catalyzed reactions. The biosynthesized dopamine is transported to vesicles via the vesicular monoamine transporter (VMAT) for storage. When a nerve impulse is conducted to the synapse, the vesicles that docked at the active zone fuse with the plasma membrane and release dopamine to the synaptic cleft. The released dopamine binds to the dopamine receptors on the membrane of the postsynaptic neuron and transmits the nerve impulse to the downstream cell. Some released dopamine will be recycled back into the cells via dopamine transporters (DAT) that localized on the membrane of the presynaptic neuron or the nearby glial cells for metabolism or reutilization. Clinical studies and experimental animal models showed that alteration of dopamine metabolism could dramatically affect physiological conditions of the subject. For example, substances abuse such as administrating amphetamine could strongly affect cognition due to the alteration of dopamine concentration in the synaptic cleft. Importantly, neurological disorders, including Parkinson's disease, depression, and other mental illness have been linked to dopamine system. Using Parkinson's disease as an example, the hallmark pathology of the patients is the neuronal loss in the substantia nigra, where most neurons use dopamine to send message to the striatum for controlling motor functions. Thus, the loss of dopaminergic neurons could significantly reduce the amount of dopamine released to the synapse and subsequently lead to parkinsonism. Therefore, it is critical to understand dopamine metabolism and function in the brain for delineating dopamine-related disorders and physiology. Dopamine is not stable under physiological condition. Indeed, dopamine measurement in vivo remains a bottleneck for neuroscientist. Currently, the most common method to analysis dopamine is using high performance liquid chromatography (HPLC) to measure the biological sample in the non-physiological condition. This method is unable to distinguish dopamine from individual neuron, or to determine whether the readout is the secreted dopamine or dopamine inside the cell. Recently, the development of multi-walled carbon nanotubes (MWCNT) takes the advantage of that each substance has specific oxidation-reduction potential after being oxidized by the carbon nanotube, thus the possible content of the tested substance can be converted by the specific potential changes of the potential. However, this method requires the injection of carbon nanotubes into the tested subject, which is invasive and only suitable for a single point measurement. Moreover, the oxidation-reduction potential of many substances in actual measurements produces overlapped readings; for instance, the oxidation-reduction potential of vitamin C overlaps with dopamine, which may hinder the specificity of this measurement since vitamin C often coexists with dopamine in vivo.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

The present invention relates to fusion proteins of monoamine oxidase B (MAO B)-green fluorescent protein (GFP) and utilizes "shield effect" to detect the dopamine under physiological condition, providing the reagent and method for dopamine detection.

DETAILED DESCRIPTION OF THE INVENTION

Figure 1:
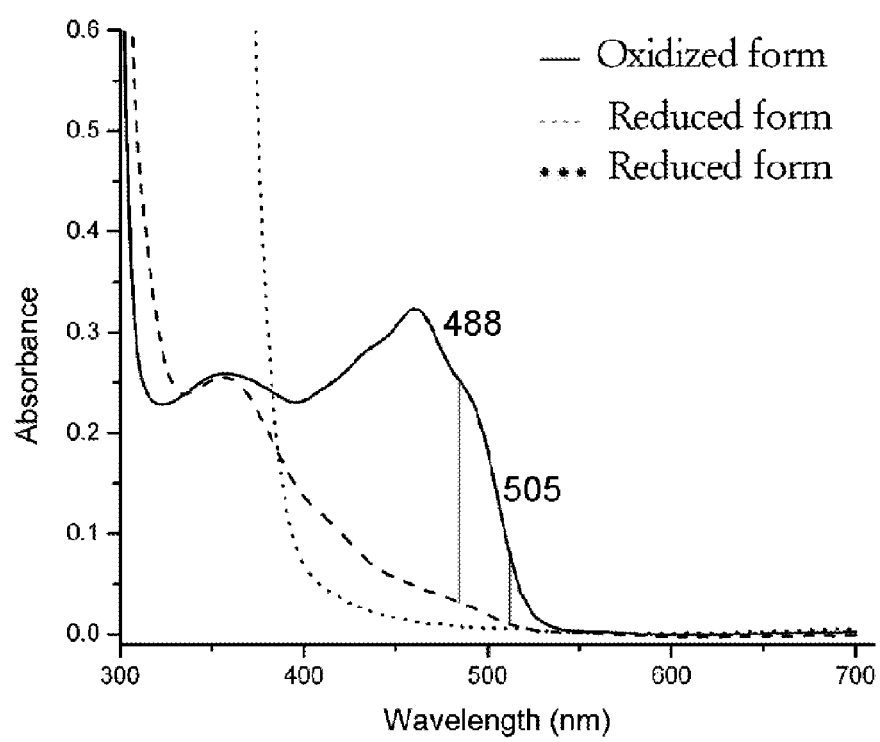
FIG. 1 shows the reaction of the oxidation state of the MAO B to specific spectrum. (-) the oxidation state; (- - -) reduced by benzylamin; ( . . . ) reduced by sodium dithionite. All the optical density (OD) was measured in the 50 mM sodium phosphate buffer with 0.5% (w/v) reduced triton X-100 (Min Li et al. (2006) *Biochemistry*, 45 (15), pp 4775-4784).

Through genetic engineering, the present invention allows the organism to produce specific probes for detecting dopamine under physiological condition. By analyzing the proteins with potential binding affinity to dopamine, the present invention selects human monoamine oxidase B (hMAO B) as the target for probe design. According to the literature, hMAO B is the enzyme by which dopamine is mainly oxidized. Biochemical and structural analyses indicate that hMAO B anchors to the mitochondrial outer membrane through its C-terminal tail and leaves its catalytic domain in the cytoplasm to bind dopamine or other substrates. It is known that hMAO B forms covalent bonds with coenzyme flavin adenine dinucleotide (FAD) after synthesized. Previous report showed that hMAO B in oxidation state can absorb light between 400 to 500 nm (FIG. 1). However, when hMAO B reacts with its substrates, it stays in the reduction state and this special light-absorbing property is substantially reduced. The present invention fuses the truncated hMAO B protein that possessing different lengths of C-terminal-deleted fragments with either a complete green fluorescence protein (GFP), or GFP that contains a small deletion from its N-terminus to form fusion proteins, or we refer as dopamine probes. Under the condition when the hMAO B remains in the oxidized form, the exposure of dopamine probes in 488 nm laser, the excitation wavelength that can trigger GFP to emit fluorescence, is absorbed by the hMAO B and thus blocking the GFP emission. However, when the substrates (like dopamine and MPTP) bind to the hMAO B in the dopamine probe, the hMAO B stays in the reduction state temporarily due to the interaction between FAD and the substrates, and such alteration substantially prohibits hMAO from absorb light and thus permits the 488 nm laser to excite the GFP fluorescence. Taking advantage of such optical properties, the probes can be used to detect the changes in the amount of dopamine under physiological condition in cells and tissues.

The present invention also provides a probe protein for dopamine detection. The probe protein comprises fusion proteins of monoamine oxidase-green fluorescent protein (MAO-GFP), and the monoamine oxidase is selected from human monoamine oxidase A or human monoamine oxidase B. In a preferred embodiment, the monoamine oxidase is selected from human monoamine oxidase B.

In the present invention, the human monoamine oxidase is selected from the protein fragment composed of the amino acids 1-462 of the sequence SEQ ID NO: 1 or the protein fragment composed of the amino acids 1-457 of the sequence SEQ ID NO: 1. In a preferred embodiment, the monoamine oxidase is selected from the protein fragment composed of the amino acids 1-462 of the sequence SEQ ID NO: 1.

In the present invention, the green fluorescent protein is selected from a complete green fluorescent protein (SEQ ID NO: 2) or a protein fragment composed of a green fluorescent protein with a 6 amino acids truncation at the N-terminus. In a preferred embodiment, the green fluorescent protein is selected from a protein fragment composed of a green fluorescent protein with a 6 amino acids truncation at the N-terminus.

In the present invention, the MAO-GFP fusion protein utilizes shield effect to detect dopamine.

As used herein, the term "shield effect" refers to the fluorescent emission of a fluorescent protein fragment that is blocked by a specific protein fragment in which can absorb the fluorescent protein's excitation light. The excitation light triggers specific fluorescent protein to emit fluorescence when the specific protein fragment's ability of absorbing excitation light is reduced. The monoamine oxidase in oxidation state absorbs light spectrum that excites the green fluorescent protein. When the monoamine oxidase is in reduction state, its ability to absorb that excitation light declined, and the green fluorescent protein is excited by the excitation light to emit green fluorescence.

As used herein, the term "oxidation state" is the state that the monoamine oxidase is not binding with substrates like dopamine, and the term "reduction state" is the state that the monoamine oxidase binds with substrates like dopamine.

As used herein, the term "excitation light" is the visible light with wavelength 400 nm-500 nm. In a preferred embodiment, the excitation light is the visible light with wavelength 488 nm.

The present invention also provides a detection reagent for detecting dopamine. Comprising the composition of this invention and the pharmaceutically acceptable carrier, the detection reagent detects the changes in the amount of dopamine under physiological condition in cells and tissues and the dopamine concentration in the samples.

The present invention also provides a method to detect dopamine, which comprises: a. providing an under test material; b. adding the detection reagent; c. providing an excitation light which excites the green fluorescent protein; and d. detecting the green fluorescent signal.

In the present invention, the under test material is selected from biological tissues or body fluids and the detection of the green fluorescent signal is performed through confocal microscopy or other fluorescent detection machines.

EXAMPLES

The examples below are non-limiting and are merely representative of various aspects and features of the present invention.

Example 1

Prevent the Fluorescent Signal of Dopamine Probe Successfully in *E. coli*

The invention transformed an empty vector DNA, the full-length GFP (SEQ ID NO: 2), the GFP with removed certain segments (ΔGFP), the complete hMAO B (SEQ ID NO: 1), the hMAO B with removed specific fragments (ΔhMAO B) (1-462 or 1-457 of the sequence SEQ ID NO: 1) and three different types (long, short, and medium forms) of probe (SEQ ID NO: 3, 4 and 5) into the *E. coli* strain BL21. After the most suitable conditions had been found, the IPTG induction was performed and vast amount of the expected proteins was produced. The Western blotting was used to detect the signals by the GFP antibody.

Result

Figure 2:
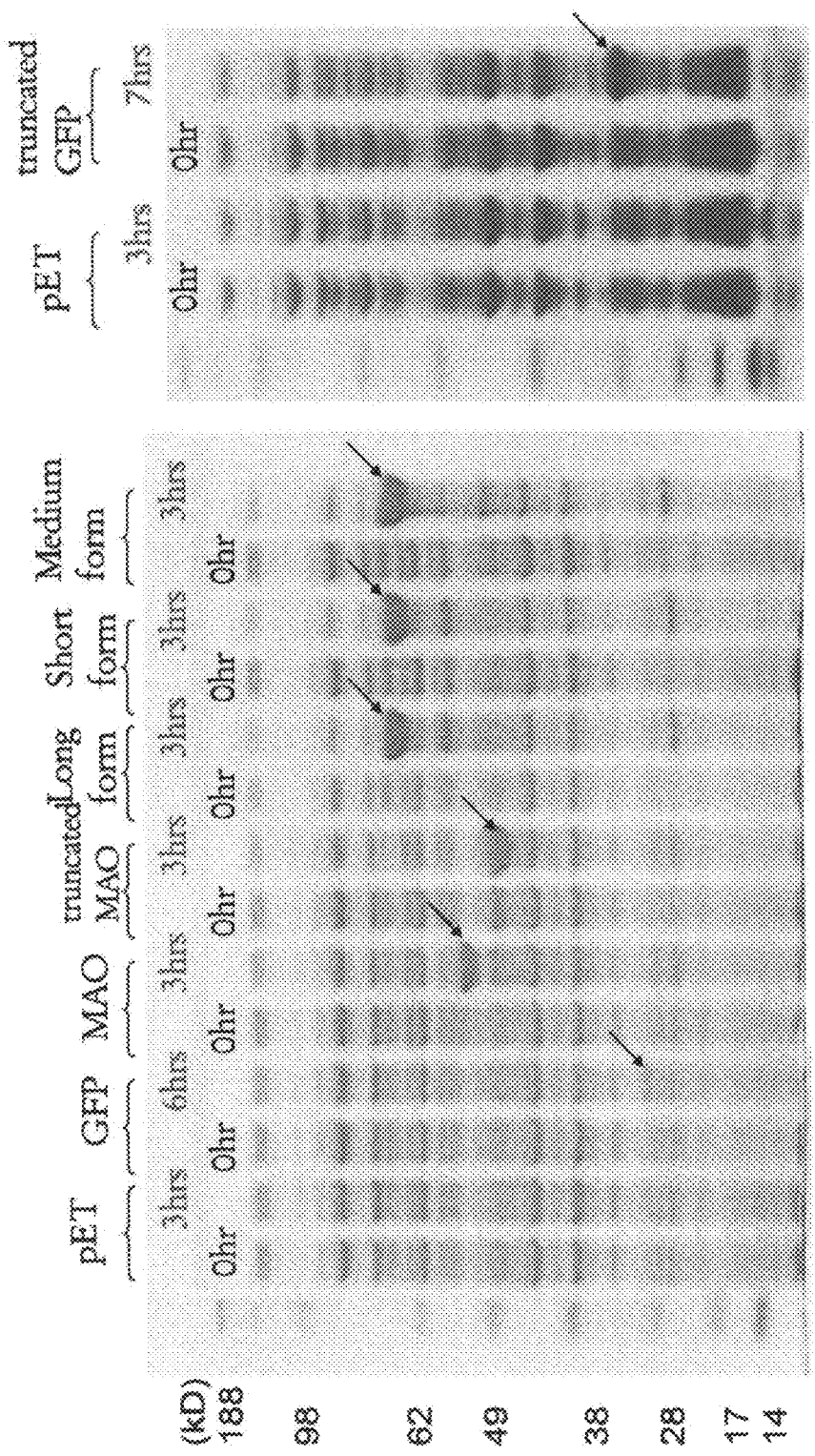
FIG. 2 shows the coomassie blue staining of SDS-PAGE after protein electrophoresis. Overexpression of dopamine probes and controls in *E. coli* BL21 after the IPTG induction; (✓) denotes clear signals in the expected molecular weight after induction.
Figure 3:
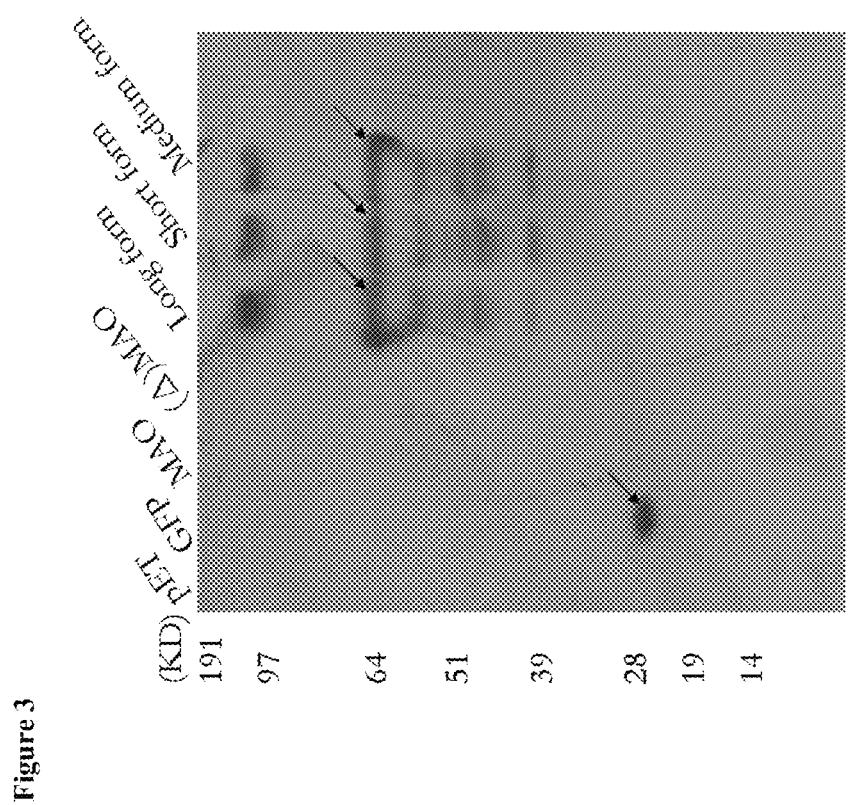
FIG. 3 shows clear signals of GFP and MAO-GFP in the expected molecular weight; (✓) denotes protein detected by the GFP antibody in a Western blotting. The pET vector and the MAO controls did not show any signal.
Figure 4:
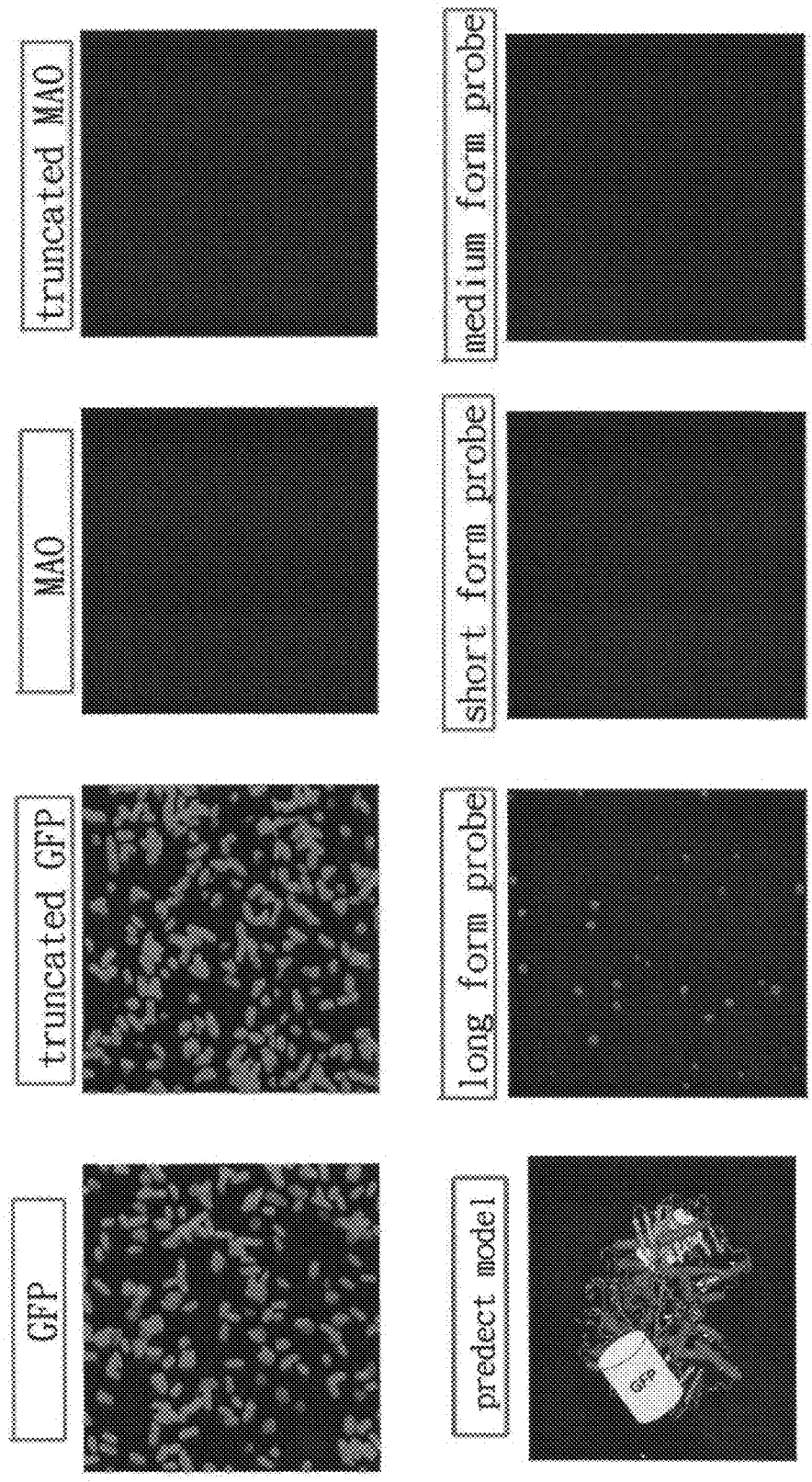
FIG. 4 shows that MAO B-GFP can block the GFP fluorescent signal. The full length GFP and the truncated GFP showed clear fluorescent signals in living BL21 after being excited by 488 nm laser under the confocal microscopy. Among the long form, short form, and medium form probes, only the long form showed detectable signal.

As shown in FIG. 2, there were significant changes before and after the induction in the expected molecular weight on the SDS gel electrophoresis. The Western blotting in FIG. 3 showed no signals of vector DNA, hMAO B and ΔhMAO B transforms. The complete GFP and three different types of probe showed strong signals when being detected by the GFP antibody. The results suggested that a large amount of the expected proteins in E. coli were successfully expressed. Evident expression of green fluorescent signal of GFP and ΔGFP in E. coli could be seen in the confocal microscope image analysis (FIG. 4), and the strains expressing hMAO B or ΔhMAO B showed no fluorescent signal. Finally, in the strains expressing the three different types of probe, only the strain with long form probe could be detected with weak fluorescent signals. Although the E. coli strains with short form and medium form probe were expressing proteins with GFP fragments, barely any fluorescent signal could be detected.

The experimental results shown above indicated that the expected proteins in E. coli BL21 strains were successfully expressed, and the signal of green fluorescent protein in hMAO B-GFP fusion protein were successfully masked by the shield effect.

Example 2

Prevent the Fluorescent Signal of Dopamine Probe Successfully in the PC12 Cell Line The rat pheochromocytoma cells (PC12 cell) were transfected with sequences of GFP, ΔhMAO B, and the probe protein through vector containing internal ribosome entry site (IRES). After antibiotic selection for more than a month, cell lines consistently expressing dopamine probe proteins were successfully established. The cell lines were detected by GFP antibody in Western blotting and observed by confocal microscopy.

Result

Figure 5:
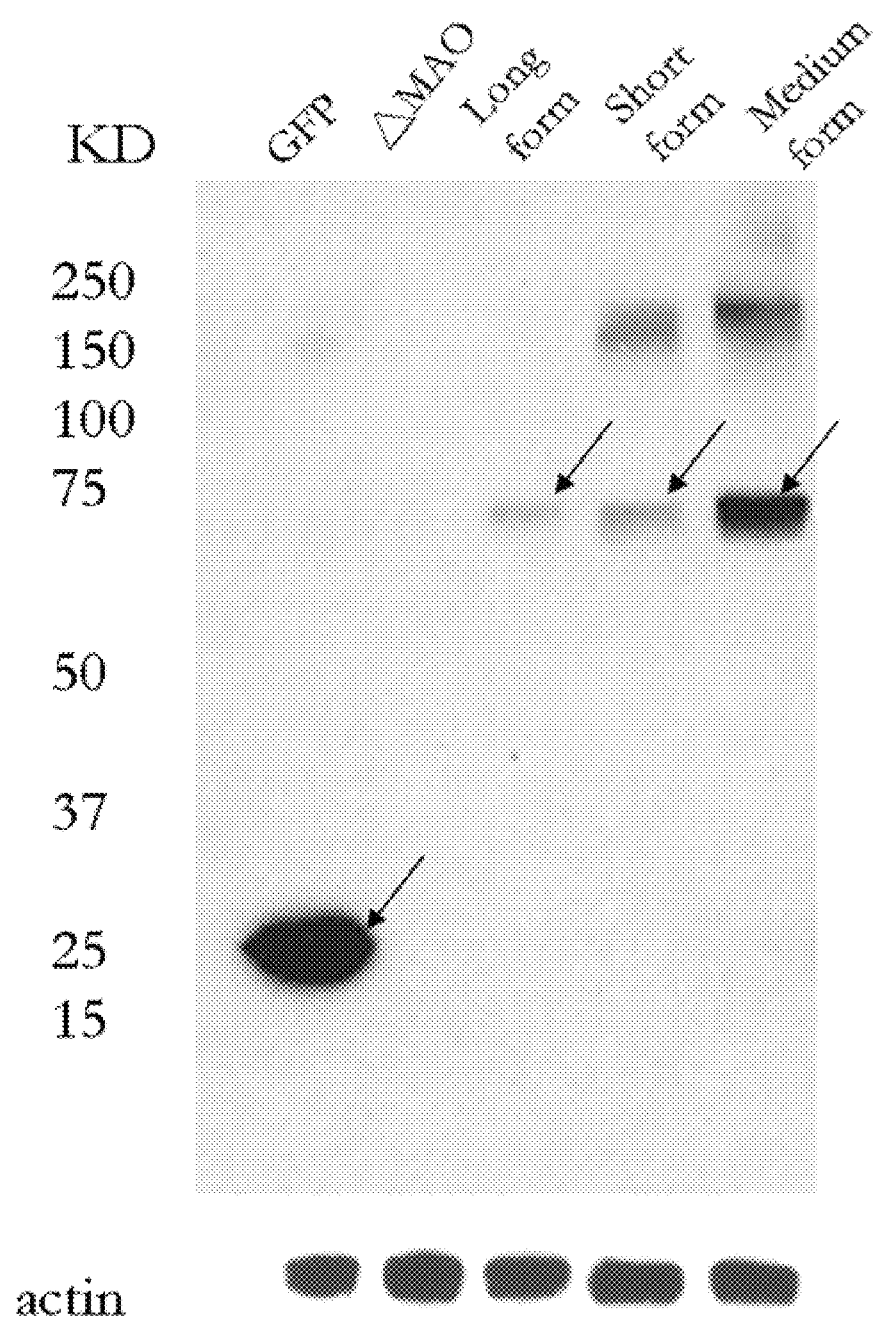
FIG. 5 shows a Western blot analysis of PC12 stable lines that expressing dopamine probes and controls. A GFP antibody detected the MAO-GFP of expected molecular weight (✓), while the truncated MAO (AMAO) control had no signal. Actin served as the loading control.
Figure 6:
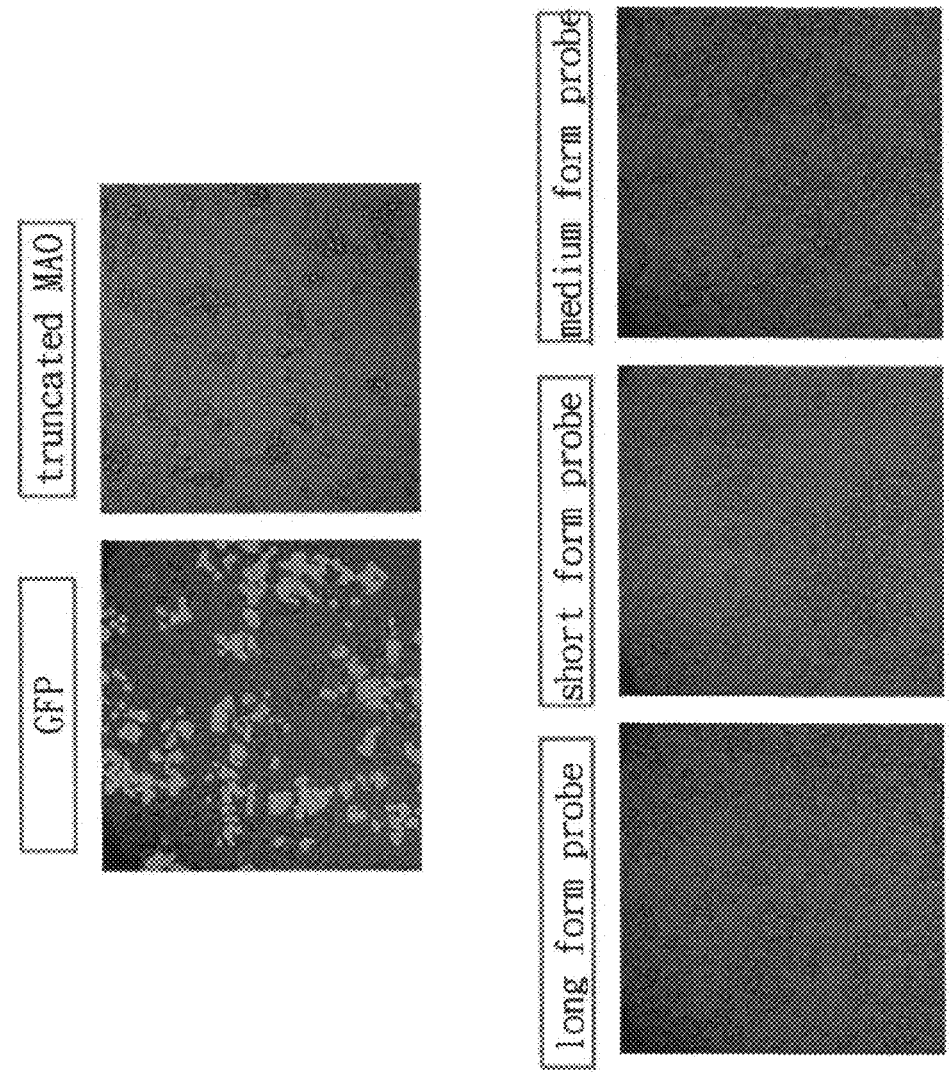
FIG. 6 shows that MAO B-GFP can block the GFP fluorescence in the undifferentiated PC12 cell line. The full length GFP showed clear fluorescent signals after being excited by 488 nm laser under the confocal microscopy, while the truncated MAO control had no signal. Among the long form, short form, and medium form probes, only the long form revealed weak, but detectable fluorescent signal.
Figure 7:
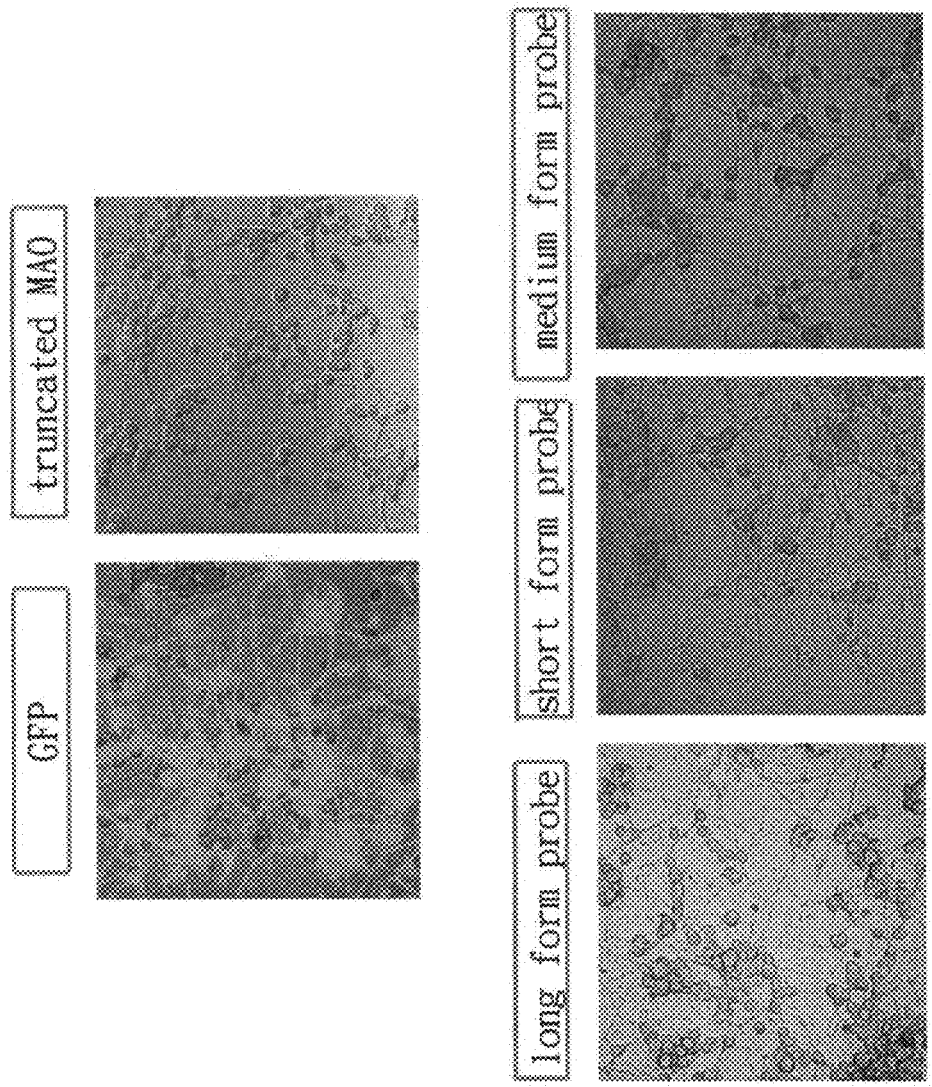
FIG. 7 shows that MAO B-GFP can block the GFP fluorescence in the differentiated PC12 cell line. The full length GFP showed clear fluorescent signals after being excited by 488 nm laser under the confocal microscopy, while the truncated MAO control had no signal. Among the probes, only the long form revealed detectable, but weak fluorescent signals.

As shown in FIG. 5, cell lines with the GFP and three different types of probe proteins showed clear signals in Western blotting, while the cell lines with hMAO B had no signal. Confocal microscope failed to detect evident GFP fluorescent signal of the hMAO B-GFP fusion proteins after excited by 488 nm laser in both the undifferentiated dopamine probe cell lines (FIG. 6) and the differentiated dopamine probe cell lines induced by nerve growth factor (NGF, FIG. 7), indicating the "shield effect" of genetic-engineered dopamine probes could successfully block the GFP excitation in the hMAO B-GFP fusion proteins.

Example 3

Test the Expression of Transporter Required for Transporting Drugs in the PC 12 Cell Line Under normal conditions, all of the tested agents such as dopamine, L-DOPA and 1-methyl-4-phenyl-1,2,3,6-tetrahydropyridine (MPTP) required the dopamine transporter (DAT) to carry them into the PC12 cells. Therefore, the immunofluorescence staining and Western blotting with DAT antibody were used to detect dopamine transporter in the differentiated and undifferentiated cell lines.

Result

Figure 8:
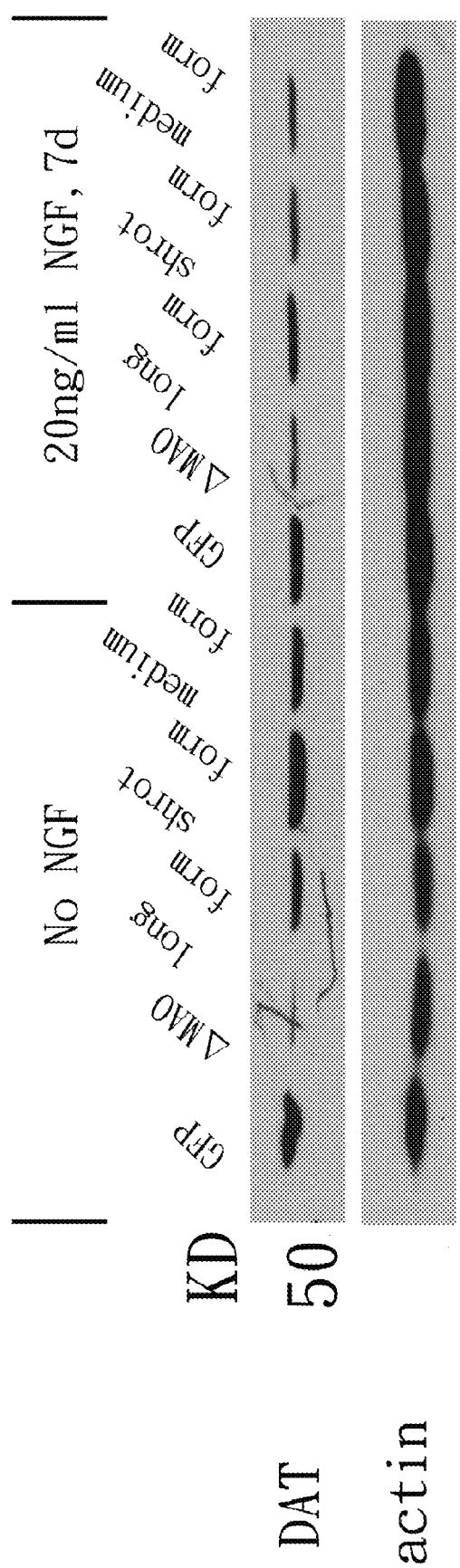
FIG. 8 shows clear signals of the dopamine transporter (DAT) in PC12 cell detected by anti-DAT antibody in a Western blotting. Actin served as the loading control.
Figure 9:
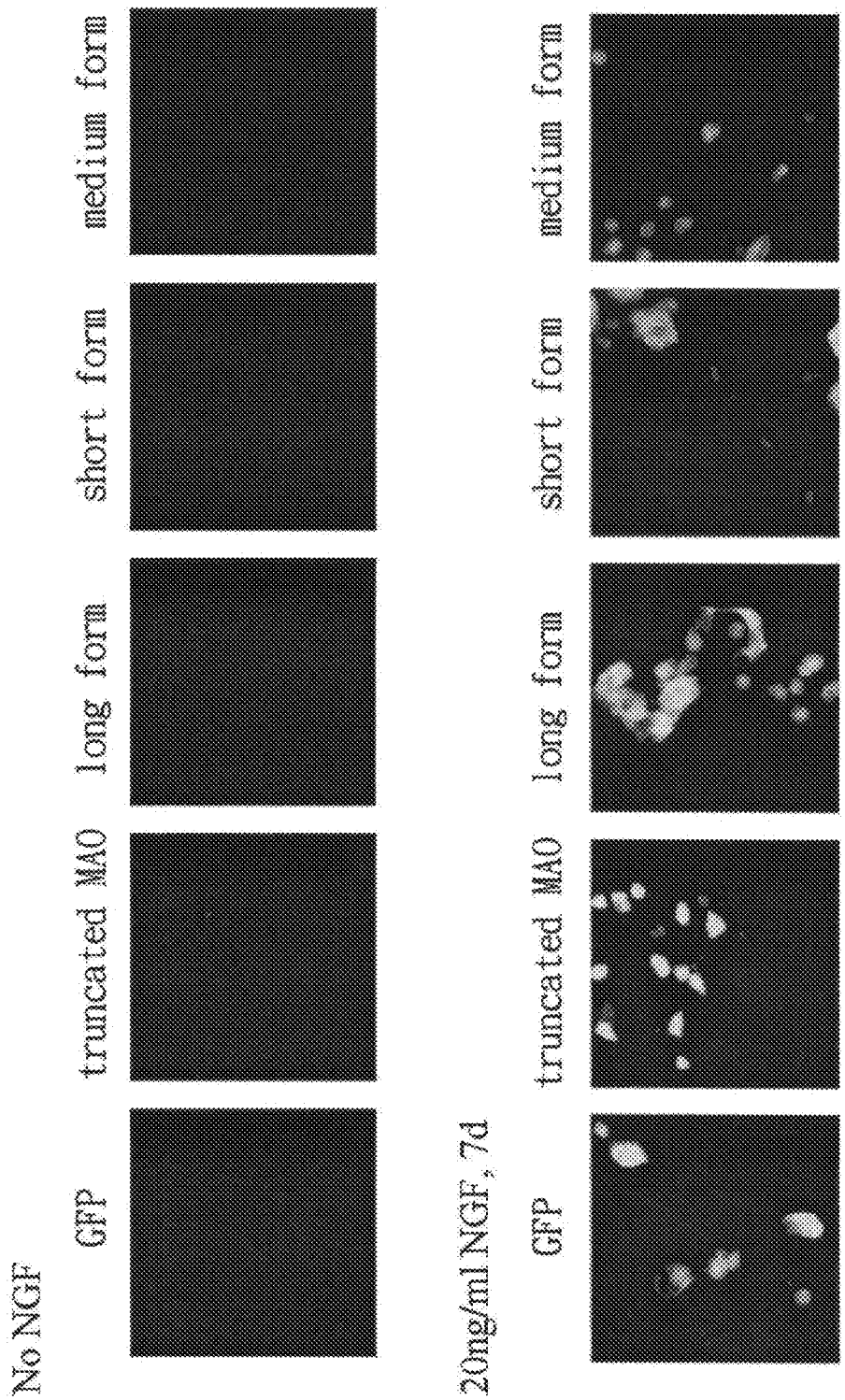
FIG. 9 shows the detection of DAT expression in the MAO B-GFP cells by immunofluorescence staining Cells were plated on collagen-coated coverslips and immunostained with anti-DAT antibody. The anti-DAT antibody detected a weak signal in undifferentiated PC12 cells (the upper row), while more robust signals could be identified in differentiated PC12 cells (the lower row).

Western blotting demonstrated that all dopamine probe cell lines as well as control expressed DAT although it seemed that the expression level of DAT in differentiated cell lines were lower than the expression level in the undifferentiated ones (FIG. 8). In addition, immunofluorescence staining of anti-DAT antibody clearly identified the signals of dopamine transporter in the cell body and part of the neurite (FIG. 9).

Example 4

The Expression of Dopamine Probe Proteins in the PC12 Cells

Figure 10:
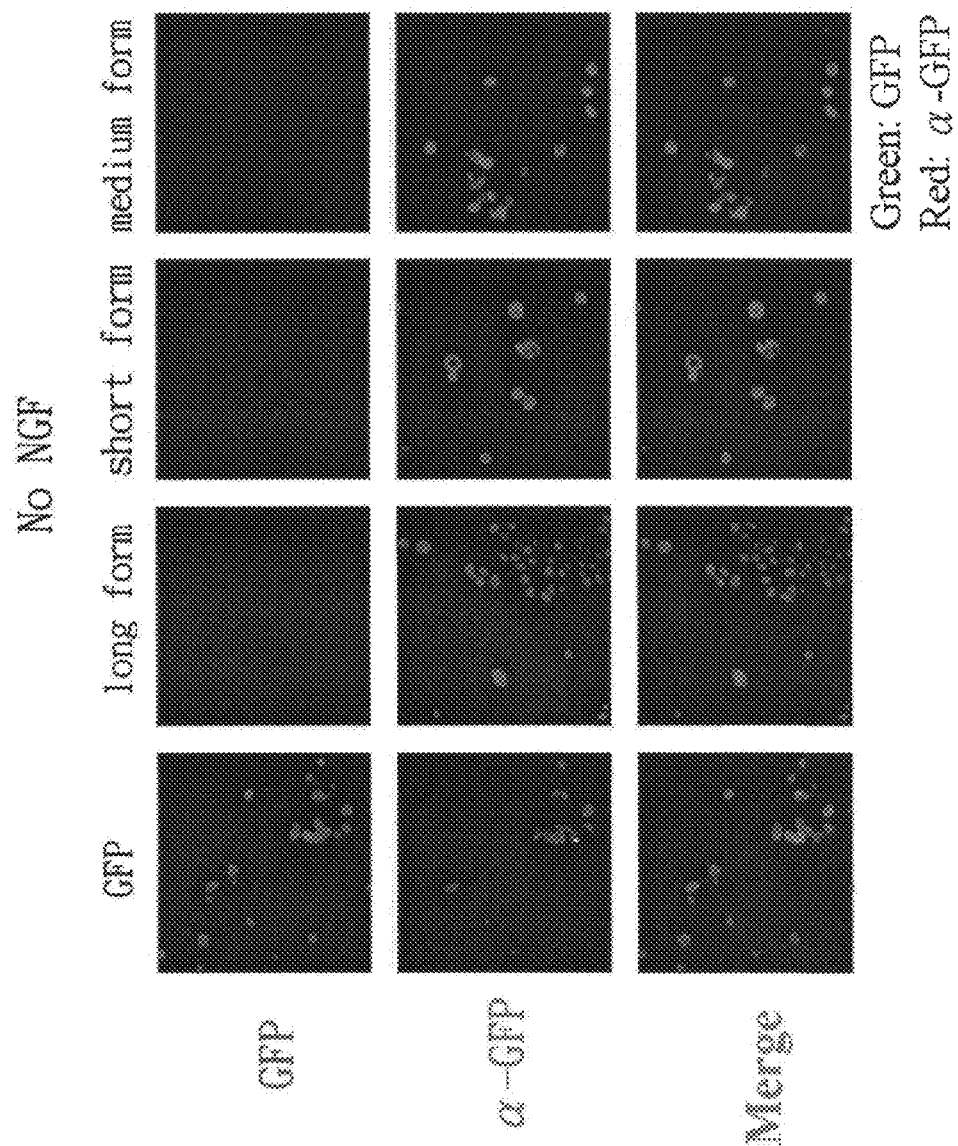
FIG. 10 shows the expression of MAO B-GFP fusion proteins in undifferentiated PC12 cell lines identified by GFP antibody. Cells were plated on collagen-coated coverslips and immunostained with anti-GFP antibody. The upper row showed that control GFP cells emitted GFP signals, but not cells expressing MAO-GFP dopamine probes. The middle row showed anti-GFP immunostaining that revealed GFP epitope in all analyzed cell lines and thus confirmed the presence of GFP protein. The lower row showed the merged images of the upper two rows.
Figure 11:
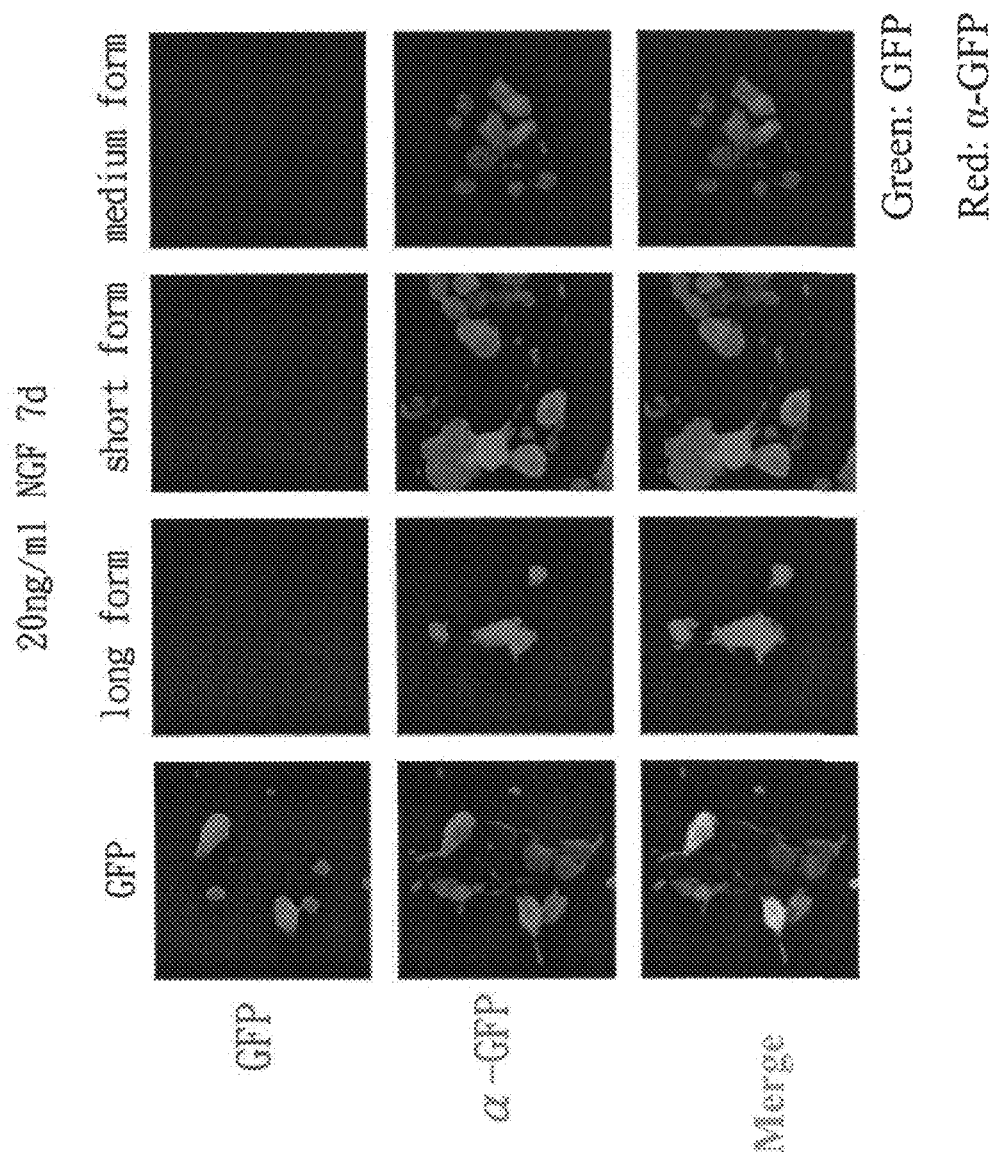
FIG. 11 shows the expression of MAO B-GFP fusion proteins in differentiated PC12 cell lines identified by GFP antibody. Cells were plated on collagen-coated coverslips, treated with NGF for 7 days, and then immunostained with anti-GFP antibody. The upper row showed that control GFP cells emitted GFP signals, but not MAO-GFP dopamine probes. The middle row showed anti-GFP immunostaining that revealed GFP epitope in all analyzed cell lines and thus confirmed the presence of GFP protein. The lower row showed the merged images of the upper two rows.
Figure 12:
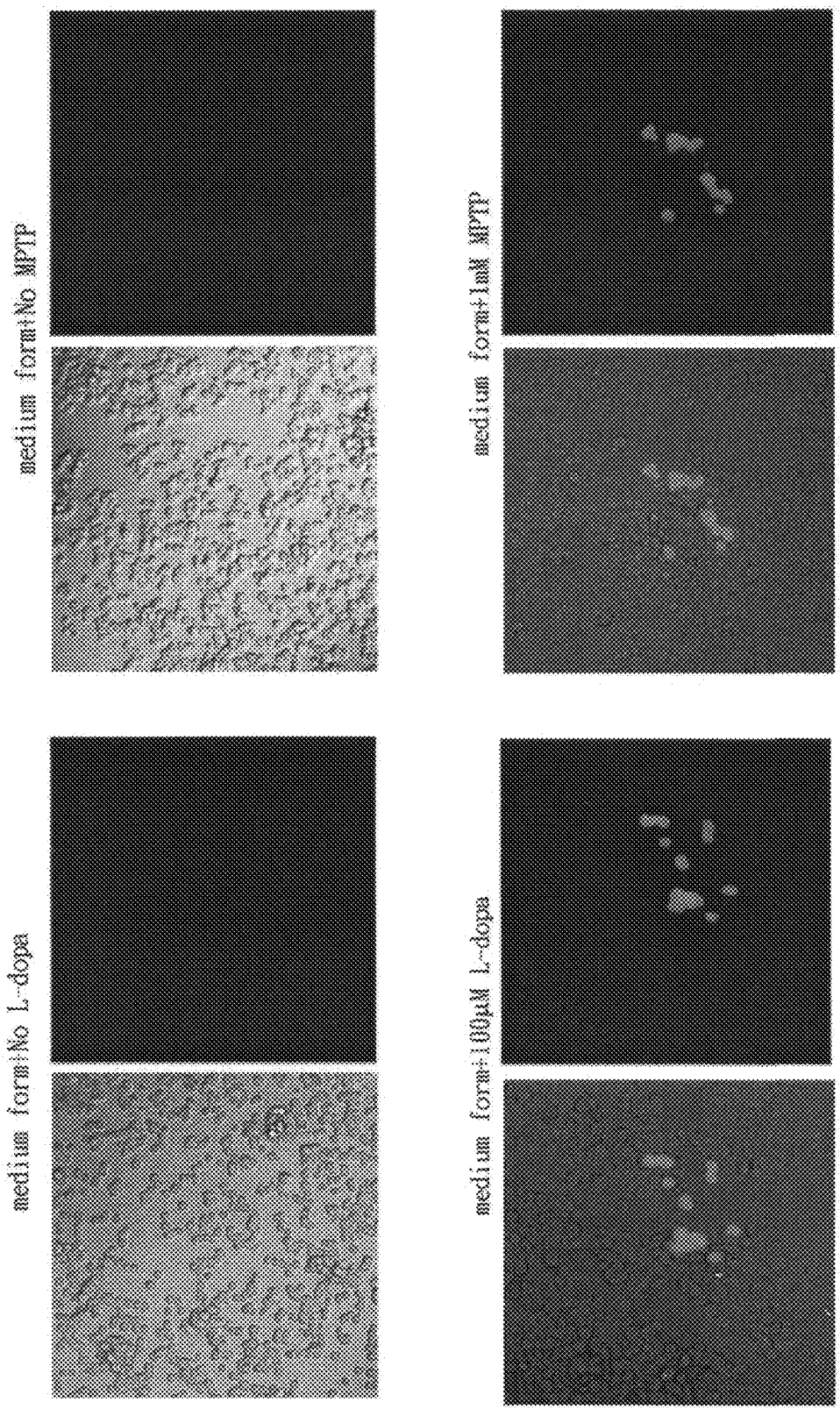
FIG. 12 shows PC12 cells that expressing the medium form of dopamine probe could reveal GFP fluorescence after the treatments of drugs that enhance dopamine level. The upper row showed that cells have barely detectable GFP signal before drug treatments. The lower row showed that some cells showed strong GFP fluorescence after treated with 100 μM L-dopa (a dopamine precursor) or 1 mM MPTP (1-methyl-4-phenyl-1,2,3,6-tetra-hydropyridine, an MAO B substrate). The paired-images on the left showed fluorescent image with bright field to reveal cell profiles.

To further confirm the reason that dopamine probe hMAO B-GFP did not release GFP fluorescence under the 488 nm laser excitation was due to the absorption of this wavelength spectrum by oxidative-state of hMAO B in the fusion protein, but not the absence of GFP protein, the immunofluorescence staining of anti-GFP was used to detect the existence of GFP protein (FIG. 10, FIG. 11).

Result

As shown in FIG. 11, although there was no direct emission of green fluorescent in cell lines expressing hMAO B-GFP, the presence of GFP fragment in the fusion protein still could be detected by immunostaining by an anti-GFP antibody in both the undifferentiated (FIG. 10) and differentiated cells (FIG. 11). The result suggested that the dopamine probe could successfully block the excitation of GFP fluorescence in the absence of substrate. According to the location of signals, the probe protein was found to express mainly in the cytoplasm of PC12 cells.

Example 5

Additions of MAO Substrates 1-methyl-4-phenyl-1,2,3,6-tetrahydropyridine (MPTP) and L-DOPA in Cells Expressing Dopamine Probe Elicit GFP Fluorescence MPTP is a widely used compound as an MAO substrate. It is also used for measuring the enzyme activity of the MAO protein. The L-DOPA is a stable dopamine precursor and has been extensively used for the treatment of Parkinson's disease. After entering the cell, it could be converted into dopamine by the dopa decarboxylase. Both of the drugs could bind to dopamine transporter and be transported into the PC12 cells.

Result

In the preliminary experiment, a part of the cells were clearly released from the "shield effect" after the excitation of 488 nm laser. The green fluorescence in those cells was successfully emitted after treating with MPTP and L-DOPA. Therefore, these results verified the effectiveness of this invention of dopamine probe.

What is claimed is:

1. A probe protein for dopamine detection, which comprises fusion proteins of monoamine oxidase-green fluorescent protein (MAO-GFP), corresponding to SEQ ID NO. 3, 4 or 5.

2. The probe protein of claim 1, wherein the fusion protein of MAO-GFP utilizes shield effect to detect dopamine.

3. The probe protein of claim 2, wherein the shield effect indicates that the fluorescence emission of a fluorescent protein fragment is blocked by a specific protein fragment which absorbs the fluorescent protein's excitation light; the excitation light excites specific fluorescent protein to show fluorescence when the ability of the specific protein fragment to absorb excitation light is reduced.

4. The probe protein of claim 3, wherein the shield effect indicates that the monoamine oxidase in oxidation state absorbs excitation light which excites the green fluorescent protein; when the monoamine oxidase is in reduction state, its ability to absorb that excitation light becomes weaker, and the green fluorescent protein is excited by the excitation light to show green fluorescence.

5. The probe protein of claim 4, wherein the oxidation state indicates the state that the monoamine oxidase does not bind a substrate.

6. The probe protein of claim 4, wherein the reduction state indicates the state that the monoamine oxidase binds a substrate.

7. The probe protein of claim 4, wherein the excitation light is the visible light with wavelength 400 nm-500 nm.

8. The probe protein of claim 7, wherein the excitation light is the visible light with wavelength 488 nm.

9. A detection reagent for detecting dopamine, which comprises the probe protein of claim 1 and a pharmaceutical acceptable carrier.

10. The detection reagent of claim 9, which detects the changes in the amount of dopamine under physiological condition in cells and tissues and the dopamine concentration in the samples.

11. A probe protein for dopamine detection, which consists of fusion proteins of monoamine oxidase-green fluorescent protein (MAO-GFP) wherein the green fluorescent protein is a protein fragment with a 6 amino acids truncation at the N terminus.

12. The probe protein of claim 11, wherein the monoamine oxidase is selected from human monoamine oxidase A or human monoamine oxidase B.

13. A detection reagent for detecting dopamine, which comprises the probe protein of claim 11 and a pharmaceutical acceptable carrier.

14. The detection reagent of claim 13, which detects the changes in the amount of dopamine under physiological condition in cells and tissues and the dopamine concentration in the samples.

* * * * *

SEQUENCE LISTING

<160> NUMBER OF SEQ ID NOS: 5

<210> SEQ ID NO 1
<211> LENGTH: 520
<212> TYPE: PRT
<213> ORGANISM: Homo sapiens

```
<220> FEATURE:
<221> NAME/KEY: mat_peptide
<222> LOCATION: (1)..(520)

<400> SEQUENCE: 1

Met Ser Asn Lys Cys Asp Val Val Val Gly Gly Gly Ile Ser Gly
1               5                   10                  15

Met Ala Ala Lys Leu Leu His Asp Ser Gly Leu Asn Val Val Val
            20                  25                  30

Leu Glu Ala Arg Asp Arg Val Gly Arg Thr Tyr Thr Leu Arg Asn
        35                  40                  45

Gln Lys Val Lys Tyr Val Asp Leu Gly Gly Ser Tyr Val Gly Pro Thr
50                  55                      60

Gln Asn Arg Ile Leu Arg Leu Ala Lys Glu Leu Gly Leu Glu Thr Tyr
65                  70                  75                  80

Lys Val Asn Glu Val Glu Arg Leu Ile His His Val Lys Gly Lys Ser
                85                  90                  95

Tyr Pro Phe Arg Gly Pro Phe Pro Pro Val Trp Asn Pro Ile Thr Tyr
            100                 105                 110

Leu Asp His Asn Asn Phe Trp Arg Thr Met Asp Met Gly Arg Glu
        115                 120                 125

Ile Pro Ser Asp Ala Pro Trp Lys Ala Pro Leu Ala Glu Glu Trp Asp
130                 135                 140

Asn Met Thr Met Lys Glu Leu Leu Asp Lys Leu Cys Trp Thr Glu Ser
145                 150                 155                 160

Ala Lys Gln Leu Ala Thr Leu Phe Val Asn Leu Cys Val Thr Ala Glu
                165                 170                 175

Thr His Glu Val Ser Ala Leu Trp Phe Leu Trp Tyr Val Lys Gln Cys
            180                 185                 190

Gly Gly Thr Thr Arg Ile Ile Ser Thr Thr Asn Gly Gly Gln Glu Arg
        195                 200                 205

Lys Phe Val Gly Gly Ser Gly Gln Val Ser Glu Arg Ile Met Asp Leu
210                 215                 220

Leu Gly Asp Arg Val Lys Leu Glu Arg Pro Val Ile Tyr Ile Asp Gln
225                 230                 235                 240

Thr Arg Glu Asn Val Leu Val Glu Thr Leu Asn His Glu Met Tyr Glu
                245                 250                 255

Ala Lys Tyr Val Ile Ser Ala Ile Pro Pro Thr Leu Gly Met Lys Ile
            260                 265                 270

His Phe Asn Pro Pro Leu Pro Met Met Arg Asn Gln Met Ile Thr Arg
        275                 280                 285

Val Pro Leu Gly Ser Val Ile Lys Cys Ile Val Tyr Tyr Lys Glu Pro
290                 295                 300

Phe Trp Arg Lys Lys Asp Tyr Cys Gly Thr Met Ile Ile Asp Gly Glu
305                 310                 315                 320

Glu Ala Pro Val Ala Tyr Thr Leu Asp Asp Thr Lys Pro Glu Gly Asn
                325                 330                 335

Tyr Ala Ala Ile Met Gly Phe Ile Leu Ala His Lys Ala Arg Lys Leu
            340                 345                 350

Ala Arg Leu Thr Lys Glu Glu Arg Leu Lys Lys Leu Cys Glu Leu Tyr
        355                 360                 365

Ala Lys Val Leu Gly Ser Leu Glu Ala Leu Glu Pro Val His Tyr Glu
370                 375                 380

Glu Lys Asn Trp Cys Glu Glu Gln Tyr Ser Gly Gly Cys Tyr Thr Thr
385                 390                 395                 400
```

```
Tyr Phe Pro Pro Gly Ile Leu Thr Gln Tyr Gly Arg Val Leu Arg Gln
            405                 410                 415

Pro Val Asp Arg Ile Tyr Phe Ala Gly Thr Glu Thr Ala Thr His Trp
            420                 425                 430

Ser Gly Tyr Met Glu Gly Ala Val Glu Ala Gly Glu Arg Ala Ala Arg
            435                 440                 445

Glu Ile Leu His Ala Met Gly Lys Ile Pro Glu Asp Glu Ile Trp Gln
            450                 455                 460

Ser Glu Pro Glu Ser Val Asp Val Pro Ala Gln Pro Ile Thr Thr Thr
465                 470                 475                 480

Phe Leu Glu Arg His Leu Pro Ser Val Pro Gly Leu Leu Arg Leu Ile
                485                 490                 495

Gly Leu Thr Thr Ile Phe Ser Ala Thr Ala Leu Gly Phe Leu Ala His
            500                 505                 510

Lys Arg Gly Leu Leu Val Arg Val
            515                 520

<210> SEQ ID NO 2
<211> LENGTH: 239
<212> TYPE: PRT
<213> ORGANISM: Aequorea victoria
<220> FEATURE:
<221> NAME/KEY: mat_peptide
<222> LOCATION: (1)..(239)

<400> SEQUENCE: 2

Met Val Ser Lys Gly Ala Glu Leu Phe Thr Gly Ile Val Pro Ile Leu
1               5                   10                  15

Ile Glu Leu Asn Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Ile Gln Glu
                85                  90                  95

Arg Thr Ile Phe Phe Glu Asp Asp Gly Asn Tyr Lys Ser Arg Ala Glu
            100                 105                 110

Val Lys Phe Glu Gly Asp Thr Leu Val Asn Arg Ile Glu Leu Thr Gly
        115                 120                 125

Thr Asp Phe Lys Glu Asp Gly Asn Ile Leu Gly Asn Lys Met Glu Tyr
130                 135                 140

Asn Tyr Asn Ala His Asn Val Tyr Ile Met Thr Asp Lys Ala Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Ile Tyr Phe Gly Phe
210                 215                 220

Val Thr Ala Ala Ala Ile Thr His Gly Met Asp Glu Leu Tyr Lys
225                 230                 235
```

-continued

```
<210> SEQ ID NO 3
<211> LENGTH: 699
<212> TYPE: PRT
<213> ORGANISM: Artificial Sequence
<220> FEATURE:
<223> OTHER INFORMATION: from E. coli
<220> FEATURE:
<221> NAME/KEY: mat_peptide
<222> LOCATION: (1)..(699)

<400> SEQUENCE: 3

Met Ser Asn Lys Cys Asp Val Val Val Gly Gly Gly Ile Ser Gly
1               5                   10                  15

Met Ala Ala Ala Lys Leu Leu His Asp Ser Gly Leu Asn Val Val
                20                  25                  30

Leu Glu Ala Arg Asp Arg Val Gly Gly Arg Thr Tyr Thr Leu Arg Asn
                35                  40                  45

Gln Lys Val Lys Tyr Val Asp Leu Gly Gly Ser Tyr Val Gly Pro Thr
50                  55                  60

Gln Asn Arg Ile Leu Arg Leu Ala Lys Glu Leu Gly Leu Glu Thr Tyr
65                  70                  75                  80

Lys Val Asn Glu Val Glu Arg Leu Ile His His Val Lys Gly Lys Ser
                85                  90                  95

Tyr Pro Phe Arg Gly Pro Phe Pro Pro Val Trp Asn Pro Ile Thr Tyr
                100                 105                 110

Leu Asp His Asn Asn Phe Trp Arg Thr Met Asp Asp Met Gly Arg Glu
                115                 120                 125

Ile Pro Ser Asp Ala Pro Trp Lys Ala Pro Leu Ala Glu Glu Trp Asp
130                 135                 140

Asn Met Thr Met Lys Glu Leu Leu Asp Lys Leu Cys Trp Thr Glu Ser
145                 150                 155                 160

Ala Lys Gln Leu Ala Thr Leu Phe Val Asn Leu Cys Val Thr Ala Glu
                165                 170                 175

Thr His Glu Val Ser Ala Leu Trp Phe Leu Trp Tyr Val Lys Gln Cys
                180                 185                 190

Gly Gly Thr Thr Arg Ile Ile Ser Thr Thr Asn Gly Gly Gln Glu Arg
                195                 200                 205

Lys Phe Val Gly Gly Ser Gly Gln Val Ser Glu Arg Ile Met Asp Leu
210                 215                 220

Leu Gly Asp Arg Val Lys Leu Glu Arg Pro Val Ile Tyr Ile Asp Gln
225                 230                 235                 240

Thr Arg Glu Asn Val Leu Val Glu Thr Leu Asn His Glu Met Tyr Glu
                245                 250                 255

Ala Lys Tyr Val Ile Ser Ala Ile Pro Pro Thr Leu Gly Met Lys Ile
                260                 265                 270

His Phe Asn Pro Pro Leu Pro Met Met Arg Asn Gln Met Ile Thr Arg
                275                 280                 285

Val Pro Leu Gly Ser Val Ile Lys Cys Ile Val Tyr Tyr Lys Glu Pro
                290                 295                 300

Phe Trp Arg Lys Lys Asp Tyr Cys Gly Thr Met Ile Ile Asp Gly Glu
305                 310                 315                 320

Glu Ala Pro Val Ala Tyr Thr Leu Asp Asp Thr Lys Pro Glu Gly Asn
                325                 330                 335

Tyr Ala Ala Ile Met Gly Phe Ile Leu Ala His Lys Ala Arg Lys Leu
                340                 345                 350
```

Ala Arg Leu Thr Lys Glu Glu Arg Leu Lys Lys Leu Cys Glu Leu Tyr
        355                 360                 365

Ala Lys Val Leu Gly Ser Leu Glu Ala Leu Glu Pro Val His Tyr Glu
    370                 375                 380

Glu Lys Asn Trp Cys Glu Glu Gln Tyr Ser Gly Gly Cys Tyr Thr Thr
385                 390                 395                 400

Tyr Phe Pro Pro Gly Ile Leu Thr Gln Tyr Gly Arg Val Leu Arg Gln
            405                 410                 415

Pro Val Asp Arg Ile Tyr Phe Ala Gly Thr Glu Thr Ala Thr His Trp
        420                 425                 430

Ser Gly Tyr Met Glu Gly Ala Val Glu Ala Gly Glu Arg Ala Ala Arg
    435                 440                 445

Glu Ile Leu His Ala Met Gly Lys Ile Gln Pro Val Met Val Ser Lys
        450                 455                 460

Gly Ala Glu Leu Phe Thr Gly Ile Val Pro Ile Leu Ile Glu Leu Asn
465                 470                 475                 480

Gly Asp Val Asn Gly His Lys Phe Ser Val Ser Gly Glu Gly Glu Gly
            485                 490                 495

Asp Ala Thr Tyr Gly Lys Leu Thr Leu Lys Phe Ile Cys Thr Thr Gly
        500                 505                 510

Lys Leu Pro Val Pro Trp Pro Thr Leu Val Thr Leu Ser Tyr Gly
    515                 520                 525

Val Gln Cys Phe Ser Arg Tyr Pro Asp His Met Lys Gln His Asp Phe
        530                 535                 540

Phe Lys Ser Ala Met Pro Glu Gly Tyr Ile Gln Glu Arg Thr Ile Phe
545                 550                 555                 560

Phe Glu Asp Asp Gly Asn Tyr Lys Ser Arg Ala Glu Val Lys Phe Glu
            565                 570                 575

Gly Asp Thr Leu Val Asn Arg Ile Glu Leu Thr Gly Thr Asp Phe Lys
        580                 585                 590

Glu Asp Gly Asn Ile Leu Gly Asn Lys Met Glu Tyr Asn Tyr Asn Ala
    595                 600                 605

His Asn Val Tyr Ile Met Thr Asp Lys Ala Lys Asn Gly Ile Lys Val
        610                 615                 620

Asn Phe Lys Ile Arg His Asn Ile Glu Asp Gly Ser Val Gln Leu Ala
625                 630                 635                 640

Asp His Tyr Gln Gln Asn Thr Pro Ile Gly Asp Gly Pro Val Leu Leu
            645                 650                 655

Pro Asp Asn His Tyr Leu Ser Thr Gln Ser Ala Leu Ser Lys Asp Pro
        660                 665                 670

Asn Glu Lys Arg Asp His Met Ile Tyr Phe Gly Phe Val Thr Ala Ala
    675                 680                 685

Ala Ile Thr His Gly Met Asp Glu Leu Tyr Lys
        690                 695

<210> SEQ ID NO 4
<211> LENGTH: 693
<212> TYPE: PRT
<213> ORGANISM: Artificial Sequence
<220> FEATURE:
<223> OTHER INFORMATION: from E. coli
<220> FEATURE:
<221> NAME/KEY: mat_peptide
<222> LOCATION: (1)..(693)

<400> SEQUENCE: 4

```
Met Ser Asn Lys Cys Asp Val Val Val Gly Gly Ile Ser Gly
1               5                   10                  15

Met Ala Ala Lys Leu Leu His Asp Ser Gly Leu Asn Val Val
                20                  25                  30

Leu Glu Ala Arg Asp Arg Val Gly Arg Thr Tyr Thr Leu Arg Asn
                35                  40                  45

Gln Lys Val Lys Tyr Val Asp Leu Gly Gly Ser Tyr Val Gly Pro Thr
    50                  55                  60

Gln Asn Arg Ile Leu Arg Leu Ala Lys Glu Leu Gly Leu Glu Thr Tyr
65                  70                  75                  80

Lys Val Asn Glu Val Glu Arg Leu Ile His His Val Lys Gly Lys Ser
                85                  90                  95

Tyr Pro Phe Arg Gly Pro Phe Pro Val Trp Asn Pro Ile Thr Tyr
                100                 105                 110

Leu Asp His Asn Asn Phe Trp Arg Thr Met Asp Met Gly Arg Glu
                115                 120                 125

Ile Pro Ser Asp Ala Pro Trp Lys Ala Pro Leu Ala Glu Glu Trp Asp
                130                 135                 140

Asn Met Thr Met Lys Glu Leu Leu Asp Lys Leu Cys Trp Thr Glu Ser
145                 150                 155                 160

Ala Lys Gln Leu Ala Thr Leu Phe Val Asn Leu Cys Val Thr Ala Glu
                165                 170                 175

Thr His Glu Val Ser Ala Leu Trp Phe Leu Trp Tyr Val Lys Gln Cys
                180                 185                 190

Gly Gly Thr Thr Arg Ile Ile Ser Thr Thr Asn Gly Gly Gln Glu Arg
                195                 200                 205

Lys Phe Val Gly Gly Ser Gly Gln Val Ser Glu Arg Ile Met Asp Leu
    210                 215                 220

Leu Gly Asp Arg Val Lys Leu Glu Arg Pro Val Ile Tyr Ile Asp Gln
225                 230                 235                 240

Thr Arg Glu Asn Val Leu Val Glu Thr Leu Asn His Glu Met Tyr Glu
                245                 250                 255

Ala Lys Tyr Val Ile Ser Ala Ile Pro Pro Thr Leu Gly Met Lys Ile
                260                 265                 270

His Phe Asn Pro Pro Leu Pro Met Met Arg Asn Gln Met Ile Thr Arg
                275                 280                 285

Val Pro Leu Gly Ser Val Ile Lys Cys Ile Val Tyr Tyr Lys Glu Pro
    290                 295                 300

Phe Trp Arg Lys Lys Asp Tyr Cys Gly Thr Met Ile Ile Asp Gly Glu
305                 310                 315                 320

Glu Ala Pro Val Ala Tyr Thr Leu Asp Asp Thr Lys Pro Glu Gly Asn
                325                 330                 335

Tyr Ala Ala Ile Met Gly Phe Ile Leu Ala His Lys Ala Arg Lys Leu
                340                 345                 350

Ala Arg Leu Thr Lys Glu Glu Arg Leu Lys Lys Leu Cys Glu Leu Tyr
                355                 360                 365

Ala Lys Val Leu Gly Ser Leu Glu Ala Leu Glu Pro Val His Tyr Glu
                370                 375                 380

Glu Lys Asn Trp Cys Glu Glu Gln Tyr Ser Gly Gly Cys Tyr Thr Thr
385                 390                 395                 400

Tyr Phe Pro Pro Gly Ile Leu Thr Gln Tyr Gly Arg Val Leu Arg Gln
                405                 410                 415
```

```
Pro Val Asp Arg Ile Tyr Phe Ala Gly Thr Glu Thr Ala Thr His Trp
            420                 425                 430

Ser Gly Tyr Met Glu Gly Ala Val Glu Ala Gly Arg Ala Ala Arg
        435                 440                 445

Glu Ile Leu His Ala Met Gly Lys Ile Gln Pro Val Glu Leu Phe Thr
450                 455                 460

Gly Ile Val Pro Ile Leu Ile Glu Leu Asn Gly Asp Val Asn Gly His
465                 470                 475                 480

Lys Phe Ser Val Ser Gly Glu Gly Glu Gly Asp Ala Thr Tyr Gly Lys
                485                 490                 495

Leu Thr Leu Lys Phe Ile Cys Thr Thr Gly Lys Leu Pro Val Pro Trp
            500                 505                 510

Pro Thr Leu Val Thr Thr Leu Ser Tyr Gly Val Gln Cys Phe Ser Arg
        515                 520                 525

Tyr Pro Asp His Met Lys Gln His Asp Phe Phe Lys Ser Ala Met Pro
    530                 535                 540

Glu Gly Tyr Ile Gln Glu Arg Thr Ile Phe Phe Glu Asp Asp Gly Asn
545                 550                 555                 560

Tyr Lys Ser Arg Ala Glu Val Lys Phe Glu Gly Asp Thr Leu Val Asn
                565                 570                 575

Arg Ile Glu Leu Thr Gly Thr Asp Phe Lys Glu Asp Gly Asn Ile Leu
            580                 585                 590

Gly Asn Lys Met Glu Tyr Asn Tyr Asn Ala His Asn Val Tyr Ile Met
        595                 600                 605

Thr Asp Lys Ala Lys Asn Gly Ile Lys Val Asn Phe Lys Ile Arg His
    610                 615                 620

Asn Ile Glu Asp Gly Ser Val Gln Leu Ala Asp His Tyr Gln Gln Asn
625                 630                 635                 640

Thr Pro Ile Gly Asp Gly Pro Val Leu Leu Pro Asp Asn His Tyr Leu
                645                 650                 655

Ser Thr Gln Ser Ala Leu Ser Lys Asp Pro Asn Glu Lys Arg Asp His
            660                 665                 670

Met Ile Tyr Phe Gly Phe Val Thr Ala Ala Ile Thr His Gly Met
        675                 680                 685

Asp Glu Leu Tyr Lys
    690

<210> SEQ ID NO 5
<211> LENGTH: 698
<212> TYPE: PRT
<213> ORGANISM: Artificial Sequence
<220> FEATURE:
<223> OTHER INFORMATION: from E. coli
<220> FEATURE:
<221> NAME/KEY: mat_peptide
<222> LOCATION: (1)..(698)

<400> SEQUENCE: 5

Met Ser Asn Lys Cys Asp Val Val Val Gly Gly Ile Ser Gly
1               5                   10                  15

Met Ala Ala Ala Lys Leu Leu His Asp Ser Gly Leu Asn Val Val
                20                  25                  30

Leu Glu Ala Arg Asp Arg Val Gly Gly Arg Thr Tyr Thr Leu Arg Asn
            35                  40                  45

Gln Lys Val Lys Tyr Val Asp Leu Gly Gly Ser Tyr Val Gly Pro Thr
        50                  55                  60
```

```
Gln Asn Arg Ile Leu Arg Leu Ala Lys Glu Leu Gly Leu Glu Thr Tyr
 65                  70                  75                  80

Lys Val Asn Glu Val Glu Arg Leu Ile His Val Lys Gly Lys Ser
                 85                  90                  95

Tyr Pro Phe Arg Gly Pro Phe Pro Val Trp Asn Pro Ile Thr Tyr
            100                 105                 110

Leu Asp His Asn Asn Phe Trp Arg Thr Met Asp Asp Met Gly Arg Glu
        115                 120                 125

Ile Pro Ser Asp Ala Pro Trp Lys Ala Pro Leu Ala Glu Glu Trp Asp
130                 135                 140

Asn Met Thr Met Lys Glu Leu Leu Asp Lys Leu Cys Trp Thr Glu Ser
145                 150                 155                 160

Ala Lys Gln Leu Ala Thr Leu Phe Val Asn Leu Cys Val Thr Ala Glu
                165                 170                 175

Thr His Glu Val Ser Ala Leu Trp Phe Leu Trp Tyr Val Lys Gln Cys
            180                 185                 190

Gly Gly Thr Thr Arg Ile Ile Ser Thr Thr Asn Gly Gly Gln Glu Arg
        195                 200                 205

Lys Phe Val Gly Gly Ser Gly Gln Val Ser Glu Arg Ile Met Asp Leu
210                 215                 220

Leu Gly Asp Arg Val Lys Leu Glu Arg Pro Val Ile Tyr Ile Asp Gln
225                 230                 235                 240

Thr Arg Glu Asn Val Leu Val Glu Thr Leu Asn His Glu Met Tyr Glu
                245                 250                 255

Ala Lys Tyr Val Ile Ser Ala Ile Pro Pro Thr Leu Gly Met Lys Ile
            260                 265                 270

His Phe Asn Pro Pro Leu Pro Met Met Arg Asn Gln Met Ile Thr Arg
        275                 280                 285

Val Pro Leu Gly Ser Val Ile Lys Cys Ile Val Tyr Tyr Lys Glu Pro
290                 295                 300

Phe Trp Arg Lys Lys Asp Tyr Cys Gly Thr Met Ile Ile Asp Gly Glu
305                 310                 315                 320

Glu Ala Pro Val Ala Tyr Thr Leu Asp Asp Thr Lys Pro Glu Gly Asn
                325                 330                 335

Tyr Ala Ala Ile Met Gly Phe Ile Leu Ala His Lys Ala Arg Lys Leu
            340                 345                 350

Ala Arg Leu Thr Lys Glu Glu Arg Leu Lys Lys Leu Cys Glu Leu Tyr
        355                 360                 365

Ala Lys Val Leu Gly Ser Leu Glu Ala Leu Glu Pro Val His Tyr Glu
370                 375                 380

Glu Lys Asn Trp Cys Glu Glu Gln Tyr Ser Gly Gly Cys Tyr Thr Thr
385                 390                 395                 400

Tyr Phe Pro Pro Gly Ile Leu Thr Gln Tyr Gly Arg Val Leu Arg Gln
                405                 410                 415

Pro Val Asp Arg Ile Tyr Phe Ala Gly Thr Glu Thr Ala Thr His Trp
            420                 425                 430

Ser Gly Tyr Met Glu Gly Ala Val Glu Ala Gly Glu Arg Ala Ala Arg
        435                 440                 445

Glu Ile Leu His Ala Met Gly Lys Ile Pro Glu Asp Glu Ile Ser Pro
450                 455                 460

Val Glu Leu Phe Thr Gly Ile Val Pro Ile Leu Ile Glu Leu Asn Gly
465                 470                 475                 480

Asp Val Asn Gly His Lys Phe Ser Val Ser Gly Glu Gly Glu Gly Asp
                485                 490                 495
```

-continued

```
Ala Thr Tyr Gly Lys Leu Thr Leu Lys Phe Ile Cys Thr Thr Gly Lys
            500                 505                 510

Leu Pro Val Pro Trp Pro Thr Leu Val Thr Thr Leu Ser Tyr Gly Val
        515                 520                 525

Gln Cys Phe Ser Arg Tyr Pro Asp His Met Lys Gln His Asp Phe Phe
        530                 535                 540

Lys Ser Ala Met Pro Glu Gly Tyr Ile Gln Glu Arg Thr Ile Phe Phe
545                 550                 555                 560

Glu Asp Asp Gly Asn Tyr Lys Ser Arg Ala Glu Val Lys Phe Glu Gly
                565                 570                 575

Asp Thr Leu Val Asn Arg Ile Glu Leu Thr Gly Thr Asp Phe Lys Glu
            580                 585                 590

Asp Gly Asn Ile Leu Gly Asn Lys Met Glu Tyr Asn Tyr Asn Ala His
        595                 600                 605

Asn Val Tyr Ile Met Thr Asp Lys Ala Lys Asn Gly Ile Lys Val Asn
    610                 615                 620

Phe Lys Ile Arg His Asn Ile Glu Asp Gly Ser Val Gln Leu Ala Asp
625                 630                 635                 640

His Tyr Gln Gln Asn Thr Pro Ile Gly Asp Gly Pro Val Leu Leu Pro
                645                 650                 655

Asp Asn His Tyr Leu Ser Thr Gln Ser Ala Leu Ser Lys Asp Pro Asn
            660                 665                 670

Glu Lys Arg Asp His Met Ile Tyr Phe Gly Phe Val Thr Ala Ala Ala
        675                 680                 685

Ile Thr His Gly Met Asp Glu Leu Tyr Lys
    690                 695
```